US00PP10355P

United States Patent [19]

Murakami

[11] Patent Number: Plant 10,355

[45] Date of Patent: Apr. 28, 1998

[54] PETUNIA PLANT NAMED 'SUNBELOCHIPI'

[75] Inventor: Yasuyuki Murakami, Shiga, Japan

[73] Assignee: Suntory Limited, Osaka, Japan

[21] Appl. No.: 751,433

[22] Filed: Nov. 20, 1996

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 6,899 | 7/1989 | Tsuda et al. | Plt./68.1 |
| P.P. 6,914 | 7/1989 | Tsuda et al. | Plt./68.1 |
| P.P. 6,915 | 7/1989 | Tsuda et al. | Plt./68.1 |
| P.P. 8,489 | 12/1993 | Hirabayashi et al. | Plt./68.1 |
| P.P. 8,768 | 6/1994 | Hirabayashi et al. | Plt./68.1 |
| P.P. 9,322 | 10/1995 | Tachibana et al. | Plt./68.1 |
| P.P. 9,341 | 10/1995 | Tachibana et al. | Plt./68.1 |
| P.P. 9,342 | 10/1995 | Sakazaki et al. | Plt./68.1 |
| P.P. 9,556 | 5/1996 | Tachibana et al. | Plt./68.1 |
| P.P. 9,557 | 5/1996 | Suzuki et al. | Plt./68.1 |
| P.P. 9,754 | 12/1996 | Suzuki et al. | Plt./68.1 |

*Primary Examiner*—James R. Feyrer
*Assistant Examiner*—Elizabeth C. Kemmerer
*Attorney, Agent, or Firm*—Burns, Doane, Swecker & Mathis, L.L.P.

[57] ABSTRACT

Disclosed herein is a petunia plant, having a semi-decumbent habit plant having long stems. The petunia plant has over-abundant branching, particularly secondary branching is strong, and great profusion blooms, the whole bush remaining in bloom for a considerable period of time. The flowers are single and very small, the petals having a vivid purplish red color, and the bottom color of the corolla throat is strong yellow and the outside color of corolla tube is light greenish yellow. The plant has a high resistance to rain, heat, drought and pest.

2 Drawing Sheets

BACKGROUND OF THE VARIETY

The present invention relates to a new and distinct variety of petunia plant obtained from the crossing of a wild type of petunia plant called "C1" (♀) native to Brazil and the other wild type of petunia plant called "C2" (♂) native to Brazil.

The petunia is a very popular plant and is used for flower bedding and potting in the summer season. There are only a few varieties of the petunia plant which do not have an upright growth habit and which have a high resistance to rain, heat, cold, and diseases. The petunia which we previously filed, i.e., the "Revolution" series [(Revolution Purplepink (U.S. Plant Pat. No. 6,915), Revolution Brilliantpink (U.S. Plant Pat. No. 6,914), Revolution Brilliantpink-mini (U.S. Plant Pat. No. 6,899)] is decumbent type plant having long stems, a lower plant height, abundant branching, and a high resistance to heat, cold and rain. However, there are only a few varieties having a great profusion of flowers, vivid purplish red color color and very small flower and a high resistance to rain, heat, cold and diseases. Accordingly, this invention was aimed at obtaining a new variety having a vivid purplish red color and very small flower, together with the above features.

The new variety of petunia plant according to this invention originated from crossing a wild type of petunia plant called "C1" (♀) native to Brazil and the other wild type of petunia plant called "C2" (♂) native to Brazil.

First of all, 167 seedling were obtained from crossing a wild type of petunia plant called "C1" as female parent and the other wild type of petunia plant called "C2" as pollen parent in November, 1992. From this crossing 15 seedlings were selected in view of decumbent habit and flower color in spring, 1993. And then 30 seedlings were obtained from a crossing of these selected 15 seedlings in summer, 1993 and were grown. Then 16 seedlings were selected from these 30 seedlings. These selected 16 seedlings were carried out a trial by flower potting and bedding. The botanically characteristics of the finally-selected 16 plants were then examined, using similar variety "Pearl Sky Blue" for comparison, from spring, 1994 to spring,1995. Finally the only one petunia plant was selected in April, 1995. As a result, it was concluded that this petunia is distinguishable from any other variety, whose existence is known to us, sufficiently uniform and stable in its characteristics, then this new variety of petunia plant was named "Sunbelchipi".

In the following description, the color-coding is in accordance with the Horticultural Color Chart of The Royal Horticultural Society, London, England (R.H.S. Color Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

The female parent use in the crossing of "Sunbelchipi" was a wild type of petunia plant called "C1" (♂) native to Brazil, the seeds of which were gathered at Gramado, Rio Grande Do Sul, Brazil and introduced to Japan in January, 1992. The petunia plant "C1" having a erect habit plant, an abundant branching, great profusion blooms, flowers are single and small, the petals having a purplish pink color, leaf shape is elliptic, and a high resistance to rain, heat, drought and pest.

The pollen parent use in the crossing of "Sunbelchipi" was other wild type of petunia plant called "C2" (♂) native to Brazil, the seeds of which were gathered at Gramado, Rio Grande Do Sul, Brazil and introduced to Japan in January, 1992. The petunia plant "C2" having a semi-decumbent habit plant having long stems, an over-abundant branching, great profusion blooms, flowers are single and very small, the petals having a reddish purple, leaf shape is lanceolate, and a high resistance to rain, heat, drought and pest. These wild type of petunia plants "C1" and "C2" are presently maintained at the Plant Biotechnology Laboratory of Suntory Ltd., residing at 863-1, Aza-Iketani, Oomori-cho, Youkaiti-shi, Shiga-ken, Japan.

The similar variety "Pearl Sky Blue" used for examination as a comparison are as follows.

Plant:
*Growth habit.*—Medium upright.
*Plant height.*—14 cm.
*Spreading area of plant.*—15–17 cm in diameter.
*Blooming period.*—April to September in the southern Kanto area, Japan.
Stem:
*Thickness.*—2.7 mm.
*Pubescence.*—Much.
*Branching.*—Abundant.
*Length of internode.*—1.3 cm.
Leaf:
*Shape.*—Elliptic.
*Length (average).*—5.5 cm.
*Width (average).*—3.5 cm.
*Color.*—Strong yellow green (R.H.S. 144A, JHS 3507).
*Pubescence.*—Much.
*Thickness.*—0.5–0.6 mm.
*Leaf attaching angle to stem.*—Horizontal to droopy.
Flower:
*Facing direction.*—Upward.
*Type.*—Single.
*Shape.*—Funnel-shape, with five-fissured limb.
*Shape of petal tip.*—Obverse.
*Waving of petal.*—Week.
*Lobation of petal.*—Shallow.
*Diameter.*—5.5 cm.
*Color.*—Petal: Strong bluish purple (R.H.S. 83C, JHS 8310). Bottom color of the corolla throat and the outside color of corolla tube: light yellow green (R.H.S. 3D, JHS 3304).
*Reproductive organs.*—1 normal pistil and 5 normal stamens.
*Peduncle.*—0.7–0.9 mm in thickness, and 2.7 cm in length.
Physiological and ecological characteristics: Moderate resistance to heat, cold and disease and pest. Strong resistance to rain.

This new and distinct variety of petunia plant, "Sunbelchipi", was asexually reproduced by cutting at the aforementioned the Plant Biotechnology Laboratory of Suntory Ltd., and the homogeneity and stability thereof were confirmed.

SUMMARY OF THE VARIETY

The new variety of petunia plant has a semi-decumbent habit, long stems and vivid purplish red flower petal and thus is very different from a similar variety, "Pearl Sky Blue". The plant has semi-decumbent habit, plant shape is compact, over-abundant branching and great profusion blooms, and the whole bush remains in bloom for a considerable period of time. Especially secondary branching is strong. The flower are single and very small, which is clearly distinguished from small flower of "Pearl Sky Blue" and the petals having a vivid purplish red, which is clearly distinguished from strong bluish purple of "Pearl Sky Blue". The bottom color of the corolla throat is strong yellow and the outside color of corolla tube is light greensih yellow. The plant has a high resistance to rain, heat, drought and pest.

DESCRIPTION OF THE VARIETY

Figure 1:
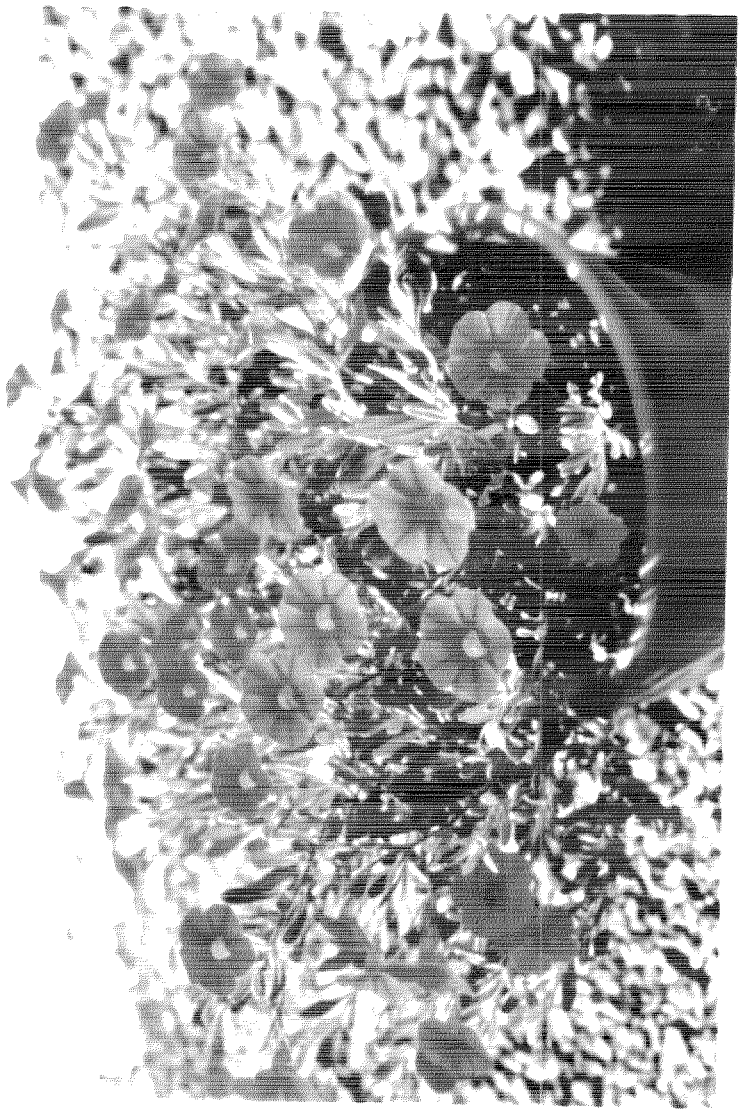
FIG. 1 is a photograph giving a partial view of the new variety of petunia plant planted in a flower pot.
Figure 2:
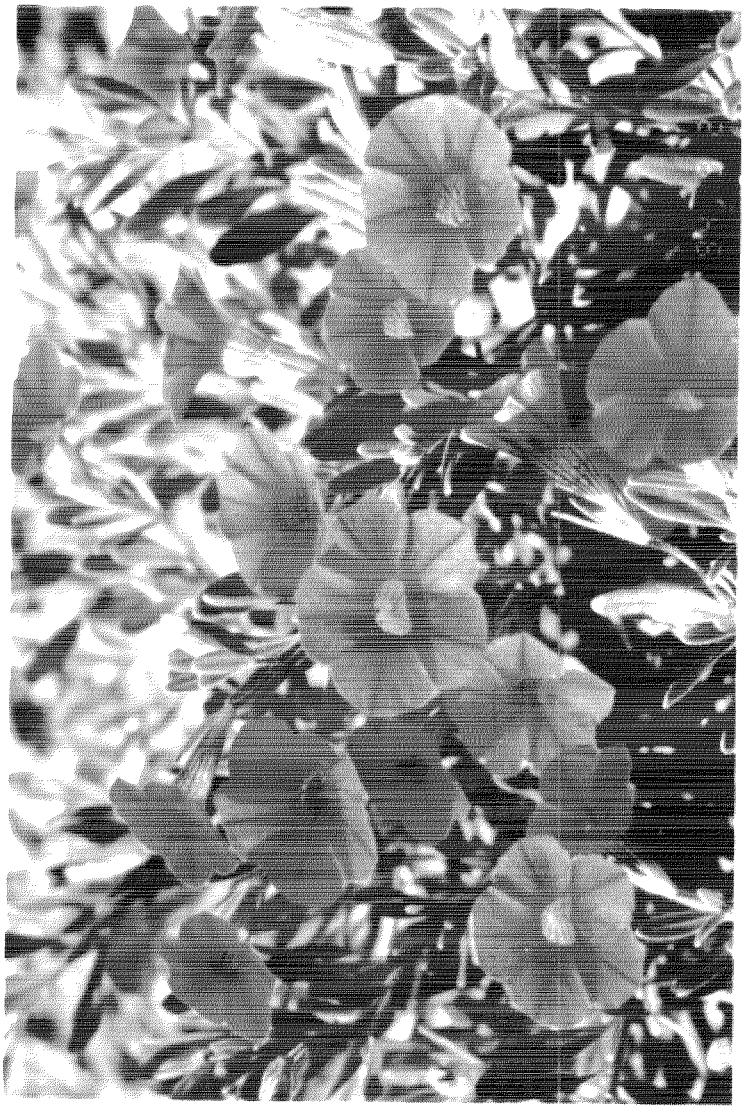
FIG. 2 is a photograph of flowers of the new variety of petunia plant.

The botanical characteristics of the new and distinct variety of petunia plant "Sunbelchipi" are as follows.

Plant:
*Growth habit.*—Decumbent to medium.
*Plant height.*—15–16 cm.
*Spreading area of plant.*—The stem extends to length of 11–13 cm from the base.
*Growth.*—Very vigorous with abundant branching, a great profusion of blooms; the whole bush remaining in bloom for a considerable this period of time.
*Blooming period.*—April to late October in the southern Kanto area, Japan. The plant shape does not change throughout this period.
Stem:
*Thickness.*—2.3 mm.
*Pubescence.*—Normal.
*Branching.*—Over-abundant. Particularly secondary branching is very strong.
*Length of internode.*—1.4 cm.
Leaf:
*Shape.*—Lanceolate.
*Length.*—5.1 cm.
*Width.*—1.6 cm.
*Color.*—Dark yellow green. (R.H.S. 146A, JHS 350 8).
*Thickness.*—0.2–0.4 mm.
*Pubescence.*—Few.
*Leaf attaching angle to stem.*—Slantly upward to horizontal.
Flower:
*Facing direction.*—Horizontal.
*Type.*—Single.
*Shape.*—Funnel-shape, with five-fissured limb.
*Shape of petal tip.*—Medium.
*Waving of petal.*—Week.
*Lobation of petal.*—Shallow.
*Diameter.*—2.8–2.9 cm.
*Color.*—Petal: Vivid purplish red (R.H.S. 57C, JHS 9707). Bottom color of the corolla throat: Strong yellow (R.H.S. 9A, JHS 2513). Outside color of corolla tube: Light greenish yellow (R.H.S. 5C, JHS 2904).
*Reproductive organs.*—1 normal pistil and 5 normal stamens. Both normal.
*Peduncle.*—0.7–0.8 mm in thickness, and 1.9 cm in length.
Physiological and ecological characteristics: High resistance to rain, heat, drought and pest, especially resistance to rain and heat is very strong.

This new variety of petunia plant is most suitable for flower bedding and potting, particularly in hanging pots or planters, and further excellent for ground cover.

The plant of this new variety "Sunbelchipi" is presently planted and maintained at the Plant Biotechnology Laboratory of Suntory Ltd., residing at 863-1, Aza-Iketani, Oomori-cho, Youkaiti-shi, Shiga-ken, Japan.

I claim:

1. A new and distinct variety of petunia plant, substantially as herein illustrated and described, characterized particularly as to novelty by (A) being a semi-decumbent habit plant having long stems, (B) an over-abundant branching, particularly secondary branching is strong, and great profusion blooms, the whole bush remaining in bloom for a considerable period of time, (C) flowers are single and very small, the petals having a vivid purplish red color, and the bottom color of the corolla throat is strong yellow and the outside color of corolla tube is light greenish yellow and (D) a high resistance to rain, heat, drought and pest.

* * * * *

1/2

SUNBELCHIPI

SUNBELCHIPI

UNITED STATES PATENT AND TRADEMARK OFFICE

CERTIFICATE OF CORRECTION

PATENT NO. : P10,355

DATED : April 28, 1998

INVENTOR(S) : Yasuyuki Murakami

It is certified that error appears in the above-identified patent and that said Letters Patent is hereby corrected as shown below:

On the title page, item [54], col. 1 line 1, change "SUNBELOCHIPI" to --"SUNBELCHIPI"--.

Signed and Sealed this

Eighth Day of September, 1998

*Attest:*

BRUCE LEHMAN

*Attesting Officer*

*Commissioner of Patents and Trademarks*